(12) United States Patent
Al-Ali

(10) Patent No.: US 9,192,329 B2
(45) Date of Patent: Nov. 24, 2015

(54) VARIABLE MODE PULSE INDICATOR

(75) Inventor: Ammar Al-Ali, Tustin, CA (US)

(73) Assignee: MASIMO CORPORATION, Irvine, CA (US)

( * ) Notice: Subject to any disclaimer, the term of this patent is extended or adjusted under 35 U.S.C. 154(b) by 551 days.

(21) Appl. No.: 11/871,808

(22) Filed: Oct. 12, 2007

(65) Prior Publication Data

US 2008/0091092 A1    Apr. 17, 2008

Related U.S. Application Data

(60) Provisional application No. 60/851,861, filed on Oct. 12, 2006.

(51) Int. Cl.
*A61B 5/02* (2006.01)
*A61B 5/1455* (2006.01)
*A61B 5/00* (2006.01)
*A61B 5/024* (2006.01)

(52) U.S. Cl.
CPC ........... *A61B 5/14551* (2013.01); *A61B 5/0002* (2013.01); *A61B 5/6826* (2013.01); *A61B 5/6838* (2013.01); *A61B 5/02438* (2013.01)

(58) Field of Classification Search
CPC . A61B 5/024; A61B 5/02416; A61B 5/02438
USPC ................................................. 600/310, 500
See application file for complete search history.

(56) References Cited

U.S. PATENT DOCUMENTS

| | | |
|---|---|---|
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |

(Continued)

OTHER PUBLICATIONS

US 8,845,543, 09/2014, Diab et al. (withdrawn)

*Primary Examiner* — Michael D'Angelo
*Assistant Examiner* — Christian Jang
(74) *Attorney, Agent, or Firm* — Knobbe, Martens, Olson & Bear LLP

(57) ABSTRACT

A user configurable variable mode pulse indicator provides a user the ability to influence outputs indicative of a pulse occurrence at least during distortion, or high-noise events. For example, when configured to provide or trigger pulse indication outputs, a pulse indicator designates the occurrence of each pulse in a pulse oximeter-derived photo-plethysmograph waveform, through waveform analysis or some statistical measure of the pulse rate, such as an averaged pulse rate. When the configured to block outputs or not trigger pulse indication outputs, a pulse indicator disables the output for one or more of an audio or visual pulse occurrence indication. The outputs can be used to initiate an audible tone "beep" or a visual pulse indication on a display, such as a vertical spike on a horizontal trace or a corresponding indication on a bar display. The amplitude output is used to indicate data integrity and corresponding confidence in the computed values of saturation and pulse rate. The amplitude output can vary a characteristic of the pulse indicator, such as beep volume or frequency or the height of the visual display spike.

9 Claims, 9 Drawing Sheets

(56) References Cited

U.S. PATENT DOCUMENTS

| | | |
|---|---|---|
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |

(56) References Cited

U.S. PATENT DOCUMENTS

| | | | |
|---|---|---|---|
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |

(56) References Cited

U.S. PATENT DOCUMENTS

| | | |
|---|---|---|
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al- Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 2002/0035315 A1* | 3/2002 | Ali et al. ............... 600/300 |
| 2002/0038094 A1* | 3/2002 | Gorman ............... 600/520 |
| 2004/0078231 A1* | 4/2004 | Wilkes et al. ............... 705/2 |
| 2009/0247984 A1 | 10/2009 | Lamego et al. |
| 2009/0275844 A1 | 11/2009 | Al-Ali |
| 2009/0299157 A1 | 12/2009 | Telfort et al. |
| 2010/0004518 A1 | 1/2010 | Vo et al. |
| 2010/0030040 A1 | 2/2010 | Poeze et al. |
| 2010/0261979 A1 | 10/2010 | Kiani |
| 2010/0317936 A1 | 12/2010 | Al-Ali et al. |
| 2011/0001605 A1 | 1/2011 | Kiani et al. |
| 2011/0082711 A1 | 4/2011 | Poeze et al. |
| 2011/0105854 A1 | 5/2011 | Kiani et al. |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0116175 A1 | 5/2012 | Al-Ali et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0265039 A1 | 10/2012 | Kiani |

(56) References Cited

U.S. PATENT DOCUMENTS

| | | |
|---|---|---|
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0025306 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0018650 A1 | 1/2015 | Al-Ali et al. |

* cited by examiner

VARIABLE MODE PULSE INDICATOR

PRIORITY CLAIM

This present application claims priority benefit under 35 U.S.C. §119(e) from U.S. Provisional Application No. 60/851,861, filed Oct. 12, 2006, entitled "Variable Mode Pulse Indicator," which is incorporated by reference herein.

CROSS-REFERENCE TO RELATED APPLICATIONS

The present application is related to U.S. Pat. No. 6,606,511, No. 6,002,952, No. 6,464,311, No. 6,684,090, No. 6,770,028, No. 6,850,788, and the continuation, continuation-in-part, and divisional applications thereof. The present application also incorporates the foregoing disclosures herein by reference.

BACKGROUND OF THE DISCLOSURE

1. Field of the Disclosure

The present disclosure relates in general to patient monitoring and in particular to oximeter patient monitors capable of monitoring one or more physiological parameters including a pulse rate from a noninvasive optical sensor.

2. Description of the Related Art

A desirable feature of patient monitors, including oximeters such as oximeters, co-oximeters, and the like, includes at least one of an audio and video indication of a pulse occurrence substantially corresponding to a patient's pulse. Such indications of a pulse occurrence may be caused by a trigger output used to initiate an audible tone "beep" or a visual pulse indication on a display.

In some systems, when signal(s) from a noninvasive optical sensor include sufficient distortion, high noise, or simply present low signal quality, pulse indications may be difficult to calculate. In some systems, the oximeter may simply determine that no pulse indication is presented to a caregiver.

In other systems, the oximeter may attempt to determine pulse occurrences during distortion, high noise, motion-induced noise, or during low signal quality or confidence. For example, in U.S. Pat. No. 6,606,511, which is assigned to Masimo Corporation ("Masimo") of Irvine, Calif., which is the assignee of the current application and incorporated by reference herein, a pulse trigger output from a rule-based processor is responsive to pulse waveforms of the patient's oximeter-derived photo-plethysmograph waveform in low-noise or no-distortion situations. However, during high-noise or distortion situations, the pulse trigger output may advantageously become dependent on an average or other statistical determination of the pulse rate. This "intelligent beep" reliably indicates the patient's pulse, yet responds to patient arrhythmias, asystole conditions and similar irregular plethysmographs. An example of the determination of pulse rate in the presence of distortion is described in U.S. Pat. No. 6,002,952, No. 6,463,311, No. 6,684,090, all of which are assigned to Masimo Corporation of Irvine, Calif., and incorporated by reference herein.

As disclosed in the '511 patent, when there is relatively no distortion corrupting a plethysmograph signal, the processor may analyze the shape of the pulses in the waveform to determine where in the waveform to generate the pulse indication. When distortion is present, looser waveform criteria can be used to determine if pulses are present. For example, when pulses are present, the pulse indication is based upon an averaged pulse rate. If no pulses are present, no indication occurs.

In the disclosed embodiment, the pulse indicator provides a trigger and amplitude output. The trigger output is used to initiate an audible tone "beep" or a visual pulse indication on a display, such as a vertical spike on a horizontal trace, a rising pulsing or constant bar display, one or more specific colors of a displayed parameter or trace, one or more LEDs or other visual elements, combinations of the same, or the like. The amplitude output is used to indicate data integrity and corresponding confidence in the computed values of saturation and pulse rate. The amplitude output can vary a characteristic of the pulse indicator, such as beep volume or frequency or the height of the visual display spike.

SUMMARY OF THE DISCLOSURE

With the acceptance of oximeter systems that output audio and visual indications of pulse occurrences, caregivers have begun to rely on assumptions they make from such audio and visual queries. For example, when a caregiver is accustomed to oximeter systems that are simply silent during signal distortion, high-noise, or low signal quality conditions, that caregiver may make potentially inaccurate assumptions about a patient monitored by oximeter systems that attempt to find pulse occurrences through noise. For example, even when an oximeter system includes an output that adjusts a visual indication of a pulse occurrence to indicate poor signal conditions or low confidence in determined parameters, the actuation of an audible beep may lead a caregiver to believe that the signal conditions, and perhaps the monitored patient, are better than they actually are. Conversely, a caregiver accustomed to a monitor that attempts to provide indications of pulse occurrences through distortion and noise, such as the oximeters disclosed in the '511 patent, may make potentially inaccurate assumptions about a patient monitored by oximeter systems that simply go silent during more difficult signal conditions.

Based at least thereon, a need exists for a configurable oximeter that allows caregivers to configure pulse occurrence indications to match their expectations. Therefore, in an embodiment of the disclosure, an oximeter includes a variable mode oximetry pulse indicator responsive to modes selected by a user or caregiver. For example, one mode may disable audio and visual pulse occurrence indications, another mode may disable one or the other, and yet another mode may enable audio and visual pulse occurrence indications during defined noisy conditions. In an embodiment, the user may cycle through or otherwise select the particular mode using user configuration menus and user input devices, such as, for example, a keypad or other user interface/input device.

BRIEF DESCRIPTION OF THE DRAWINGS

A general architecture that implements the various features of the disclosure will now be described with reference to the drawings. The drawings and the associated descriptions are provided to illustrate embodiments of the disclosure and not to limit its scope.

DETAILED DESCRIPTION OF THE PREFERRED EMBODIMENT

Embodiments of the present disclosure include a user configurable oximetry pulse indicator. For example, a user may configure whether one or more of audio and visual indicators of pulse occurrences is presented to a caregiver during, for example, distortion, motion-induced noise, low signal quality, or other challenging signal conditions. In an embodiment, a first mode presents audio and visual indicators of a patient's pulse to a caregiver during challenging signal conditions, while a second and third mode presents one or the other respectively, and a fourth mode blocks or otherwise diminishes the influence of the audio and visual indicators.

In an embodiment, an enable signal is generated according to the user's configurations and a pulse indicator is responsive to the enable signal. For example, a pulse indicator may advantageously determine a pulse occurrence and generate an indicator trigger. Depending upon the particular mode configured by the user, the pulse indicator trigger, and in some embodiments, a pulse indicator amplitude may advantageously be forwarded to tone and display generators. Alternatively, depending upon the particular mode, the indicator trigger and indicator amplitude may be partially or entirely blocked or otherwise diminished to match expectations of the caregiver in challenging signal conditions.

To facilitate a further understanding of the disclosure, the remainder of the description describes the invention with reference to specific drawings. Moreover, in this application, reference may be made to many blood parameters. Some references that have common shorthand designations are referenced through such shorthand designations. For example, as used herein, HbCO designates carboxyhemoglobin, HbMet designates methemoglobin, Hbt designates total hemoglobin, $SpO_2$ designates functional arterial saturation, and $SpaO_2$ designates fractional arterial saturation. Other shorthand designations such as COHb, MetHb, and tHb are also common in the art for these same constituents. These constituents are generally reported in terms of a percentage, often referred to as saturation, relative concentration, concentration, or fractional saturation. Total hemoglobin is generally reported as a concentration in g/dL. The use of the particular shorthand designators presented in this application does not restrict the term to any particular manner in which the designated constituent is reported.

Figure 1A:
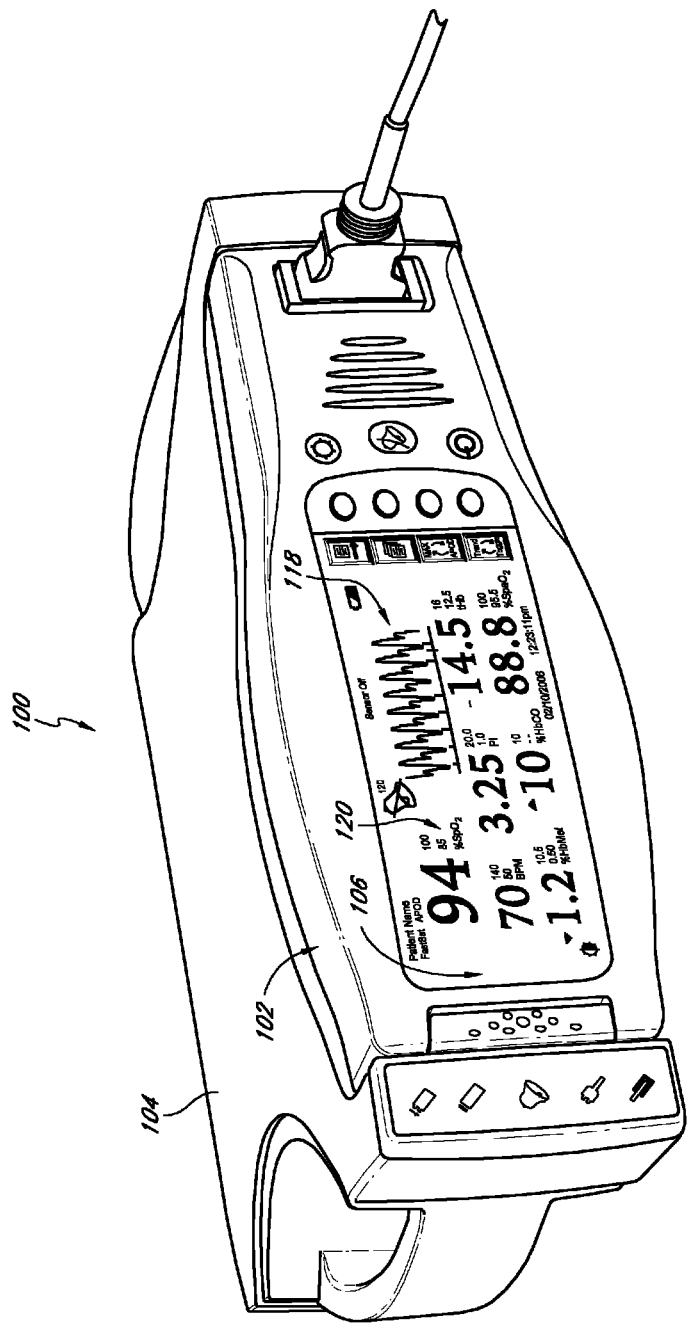
FIGS. 1A-1D illustrate various exemplary oximeter patient monitoring systems.

FIG. 1A illustrates a perspective view of a patient monitor system 100, according to an embodiment of the present disclosure. The system 100 includes a portable patient monitor 102 capable of noninvasively determining one or more physiological parameters. In an embodiment, the portable patient monitor 102 mechanically and electrically mates with a docking station 104 to recharge batteries, upload and download information, upgrade software or firmware, communicate with other monitors or the like. Disclosures of various docking stations are disclosed with reference to U.S. Pat. No. 6,770,028, incorporated above.

FIG. 1A also illustrates the monitor 102 comprising one or more displays 106 capable displaying of a wide variety of measured values in a manner that provides for quick and efficient conveyance of information to a caregiver. For example, the display 106 displays values for HbCO, HbMet, MbT, $SpO_2$, $SpaO_2$, beats-per-minute, scaled plethysmograph data 118, PI™ 120 and other information.

Figure 1B:
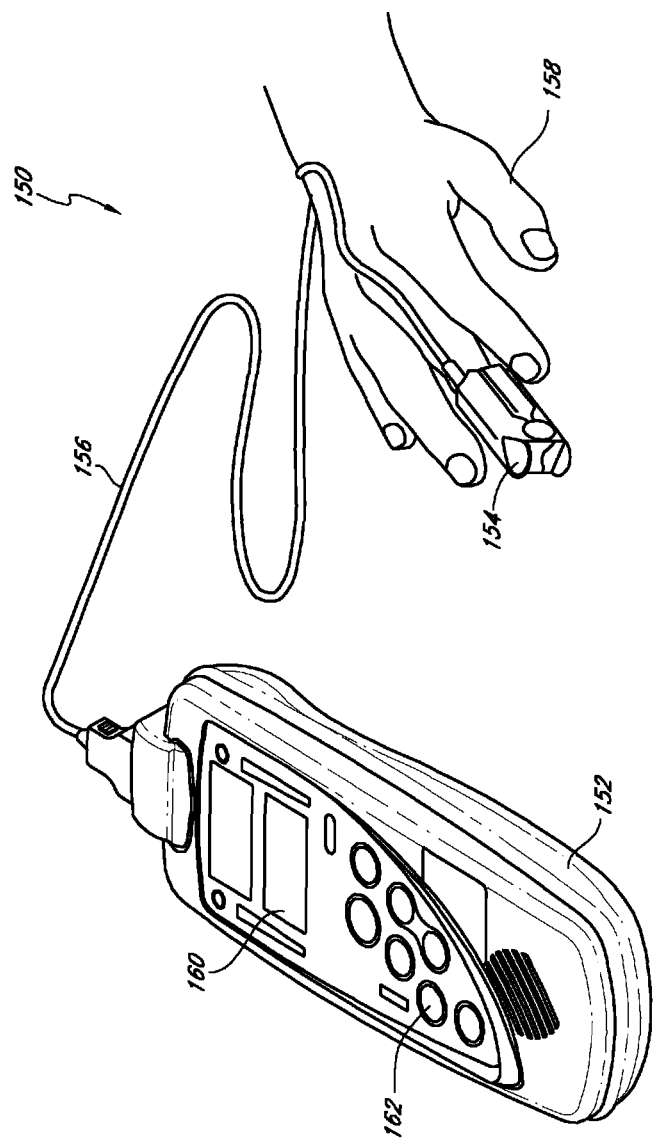

FIG. 1B illustrates a perspective view of a monitoring system 150 including a handheld noninvasive multi-parameter patient monitor 152 communicating with a reusable optical sensor 154 through a patient cable 156, according to embodiments of the disclosure. In general, the monitor 152 drives the sensor 154 to emit light of differing wavelengths into the body tissue 158. The sensor 154 detects the light after attenuation by the body tissue 158 and outputs a signal indicative of the amount of light received by the sensor 154 through the cable 156. In addition, in some embodiments, the monitor 152 communicates with a temperature sensor and a memory device associated with one or more of the sensor 154 and the cable 156, through the cable 156.

In an embodiment, the monitors 102, 152 receive sensor output and determine continuous and non-invasive measurements of a wide variety of blood parameters. Although disclosed with reference to portable monitors 102, 152, an artisan will recognize from the disclosure herein that aspects of the present disclosure can be adopted into tabletop monitors, wireless sensors, or other patient-wearable personal monitors, or multi-parameter patient monitors.

FIG. 1B also shows the sensor 154 comprising a reusable sensor in the form a clip including a spring biased pivot point capable of removably attaching the reusable sensor to a patient's finger 158. Although disclosed with reference to a reusable sensor having a spring, an artisan will recognize from the disclosure herein that the sensor 154 can advantageously comprise a disposable adhesive type sensor, a combination sensor including reusable and disposable components, components incorporated into other medical devices such as catheters, or the like, or other reusable sensor designs. Moreover, the artisan will recognize from the disclosure herein that the sensor 154 can comprise mechanical structures, adhesive or other tape structures, Velcro wraps or combination structures specialized for the type of patient, type of monitoring, type of monitor, or the like. In an embodiment, the sensor 154 provides data to the monitors 102, 152 and vice versa through the cable 156, although such communication can advantageously be wireless, over public or private networks or computing systems or devices, through intermediate medical or other devices, combinations of the same, or the like.

In an embodiment, the monitor 152 includes one or more displays 160 capable of displaying, for example, one or more of the foregoing parameters. For example, the display 160 may provide an indication of HbCO, HbMet, Hbt, $SpO_2$, $SpaO_2$, pulse rate, plethysmographs, historical or trending data, confidence or perfusion indicators, or the like. The monitors 102, 152 may include one or more audio, visual or messaging (pagers, emails, instant and phone messages, vocally presented numbers, messages and alarms, voice-over-IP ("VOIP") interfaces and functionality, or the like) alarms, user input keypad 160, or the like.

Although described in terms of certain embodiments, other embodiments or combination of embodiments will be apparent to those of ordinary skill in the art from the disclosure herein. For example, the monitors 102, 152 may combine other information with intensity-derived information to influence diagnoses or device operation. For example, patterns or changes in the continuous noninvasive monitoring of intensity-derived information may cause the activation of other vital sign measurement devices, such as, for example, blood pressure cuffs.

Figure 1C:
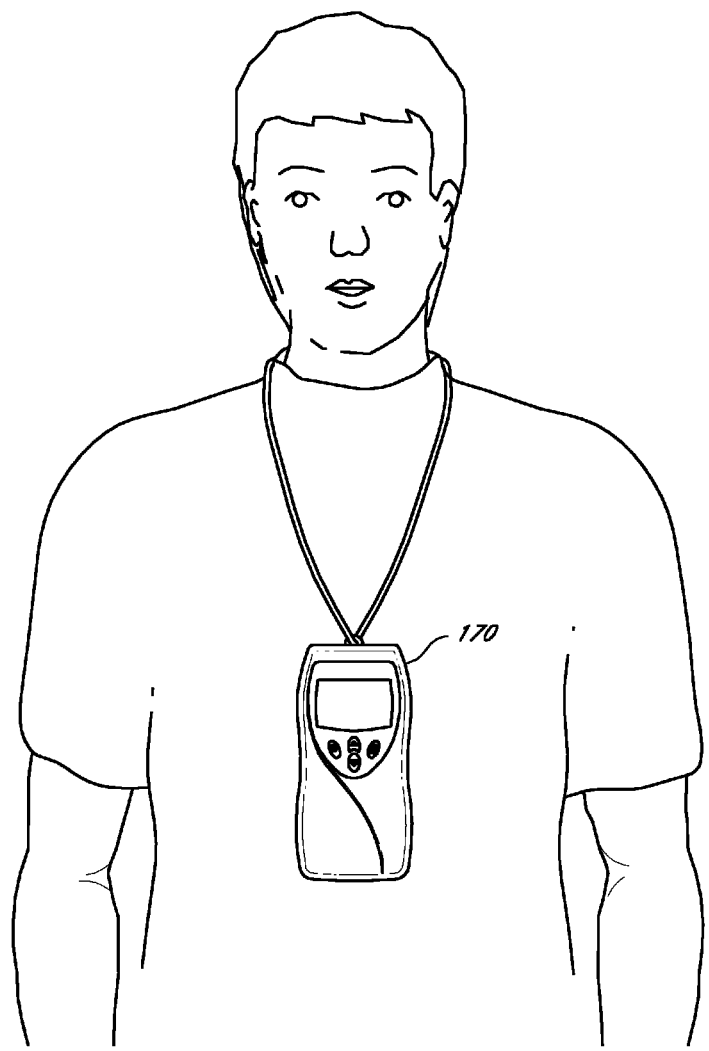

FIG. 1C illustrates a perspective view of a monitoring system including a personal or wearable noninvasive multi-parameter patient monitor 170, according to embodiments of the disclosure. Such personal oximeters 170 generally wirelessly communicated with a monitoring station to provide the monitoring station with measurements for some or all of the physiological parameters measurable by the monitor. In an embodiment, the monitor travels with a patient as the patient, for example, moves through a care site such as a hospital. Wireless networks incorporating such personal pulse technologies are commercially available from Masimo marketed under the brand RadNet™, RadLink™ and Patient Safety Net™.

Figure 1D:
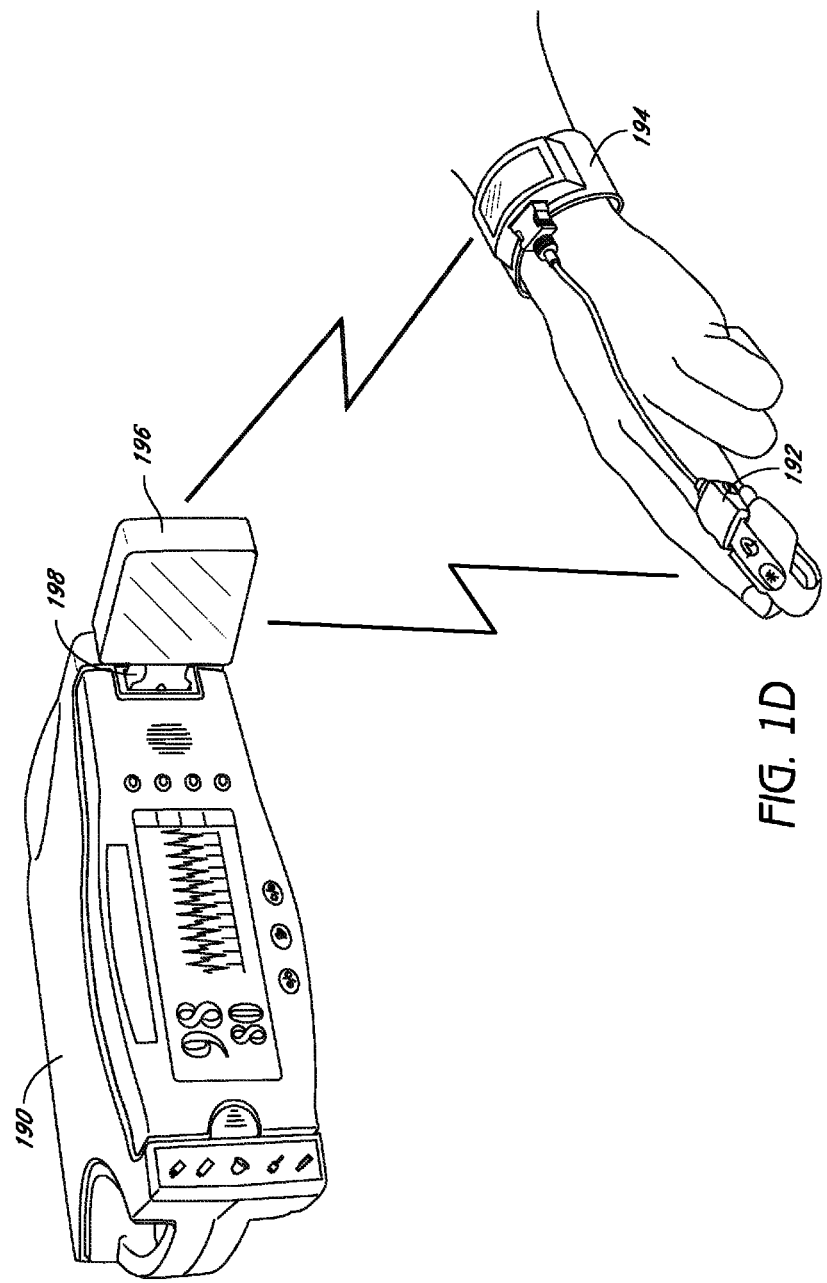

FIG. 1D illustrates a perspective view of a monitoring system including a wireless noninvasive multi-parameter patient monitor 190, according to embodiments of the disclosure. In an embodiment, a traditional sensor 192 communicates with a wireless transmission device 194 wearable, for example, on the wrist. In other embodiments, the wireless transmission device may advantageously be incorporated into a sensor housing adapted for wireless communication. In an embodiment, a wireless receiver 196 communicates with a sensor port 198 in the same manner as a wired sensor. Thus, in an exemplary embodiment shown in FIG. 1D, a traditional sensor 192 and a traditional sensor port 198 may be unaware that a patient cable has been replaced with wireless transmissions. Disclosure of wireless technologies is disclosed in U.S. Pat. No. 6,850,788, incorporated by reference herein.

Figure 2:
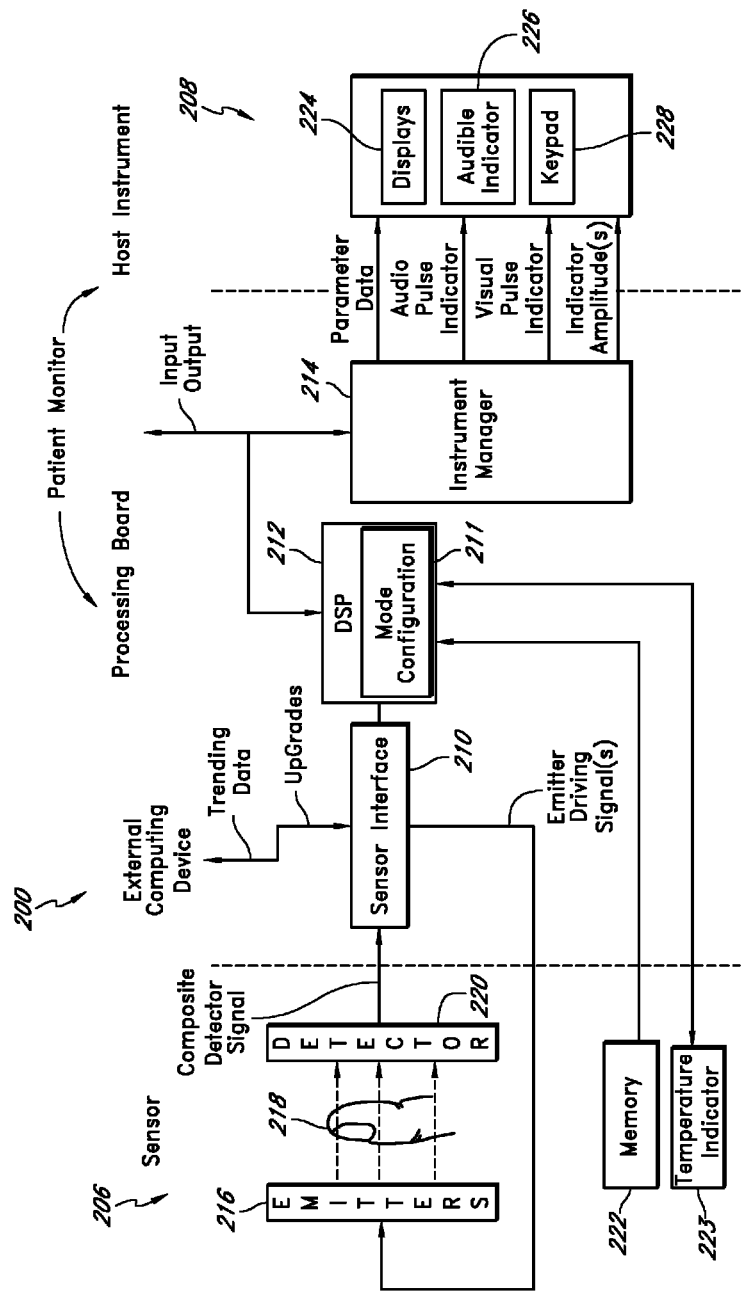
FIG. 2 illustrates an exemplary block diagram of one or more of the oximeter patient monitoring systems of FIG. 1.

FIG. 2 illustrates an exemplary block diagram of an embodiment of a patient monitoring system 200. As shown in FIG. 2, the system 200 includes a patient monitor 202 comprising a processing board 204 and a host instrument 208. The processing board 204 communicates with a sensor 206 to receive one or more intensity signal(s) indicative of one or more parameters of tissue of a patient. The processing board 204 also communicates with a host instrument 208 to display determined parameter values calculated using the one or more intensity signals. According to an embodiment, the board 204 comprises processing circuitry arranged on one or more printed circuit boards capable of installation into the monitor 202, or capable of being distributed as some or all of one or more OEM components for a wide variety of host instruments monitoring a wide variety of patient information. In an embodiment, the processing board 202 comprises a sensor interface 210, a digital signal processor and signal extractor ("DSP" or "processor") 212, and an instrument manager 214. In general, the sensor interface 210 converts digital control signals into analog drive signals capable of driving sensor emitters, and converts composite analog intensity signal(s) from light sensitive detectors into digital data.

In an embodiment, the sensor interface 210 manages communication with external computing devices. For example, in an embodiment, a multipurpose sensor port (or input/output port) is capable of connecting to the sensor 206 or alternatively connecting to a computing device, such as a personal computer, a PDA, additional monitoring equipment or networks, or the like. When connected to the computing device, the processing board 204 may upload various stored data for, for example, off-line analysis and diagnosis. The stored data may comprise trend data for any one or more of the measured parameter data, plethysmograph waveform data acoustic sound waveform, or the like. Moreover, the processing board 204 may advantageously download from the computing device various upgrades or executable programs, may perform diagnosis on the hardware or software of the monitor 202. In addition, the processing board 204 may advantageously be used to view and examine patient data, including raw data, at or away from a monitoring site, through data uploads/downloads, or network connections, combinations, or the like, such as for customer support purposes including software maintenance, customer technical support, and the like.

As shown in FIG. 2, the digital data is output to the DSP 212. According to an embodiment, the DSP 212 comprises a processing device based on the Super Harvard ARChitecture ("SHARC"), such as those commercially available from Analog Devices. However, a skilled artisan will recognize from the disclosure herein that the DSP 212 can comprise a wide variety of data and/or signal processors capable of executing programs for determining physiological parameters from input data. In particular, the DSP 212 includes program instructions capable of receiving multiple channels of data related to one or more intensity signals representative of the absorption (from transmissive or reflective sensor systems) of a plurality of wavelengths of emitted light by body tissue. In an embodiment, the DSP 212 accepts data related to the absorption of two (2) to eight (8) wavelengths of light, although an artisan will recognize from the disclosure herein that the data can be related to the absorption of two (2) to sixteen (16) or more wavelengths.

FIG. 2 also shows the processing board 204 including the instrument manager 214. According to an embodiment, the instrument manager 214 may comprise one or more microcontrollers controlling system management, including, for example, communications of calculated parameter data and the like to the host instrument 208. The instrument manager 214 may also act as a watchdog circuit by, for example, monitoring the activity of the DSP 212 and resetting it when appropriate.

The sensor 206 may comprise any commercially available noninvasive oximetry sensor. In an embodiment, the sensor 206 provides data to the board 204 and vice versa through, for example, a patient cable. An artisan will also recognize from the disclosure herein that such communication can be wireless, over public or private networks or computing systems or devices, or the like.

As shown in FIG. 2, the sensor 206 includes a plurality of emitters 216 irradiating the body tissue 218 with differing wavelengths of light, and one or more detectors 220 capable of detecting the light after attenuation by the tissue 218. The sensor 206 may also include other electrical components such as, for example, a memory device 222 comprising an EPROM, EEPROM, ROM, RAM, microcontroller, combinations of the same, or the like. In an embodiment, other sensor components may include a temperature determination device 223 or other mechanisms for, for example, determining real-time emission wavelengths of the emitters 216.

The memory 222 may advantageous store some or all of a wide variety data and information, including, for example, information on the type or operation of the sensor 206; type or identification of sensor buyer or distributor or groups of buyer or distributors, sensor manufacturer information, sensor characteristics including the number of emitting devices, the number of emission wavelengths, data relating to emission centroids, data relating to a change in emission characteristics based on varying temperature, history of the sensor temperature, current, or voltage, emitter specifications, emitter drive requirements, demodulation data, calculation mode data, the parameters for which the sensor is capable of supplying sufficient measurement data (e.g., HpCO, HpMet, Hbt, or the like), calibration or parameter coefficient data, software such as scripts, executable code, or the like, sensor electronic elements, whether the sensor is a disposable, reusable, multi-site, partially reusable, partially disposable sensor, whether it is an adhesive or non-adhesive sensor, whether the sensor is a reflectance, transmittance, or transreflectance sensor, whether the sensor is a finger, hand, foot, forehead, or ear sensor, whether the sensor is a stereo sensor or a two-headed sensor, sensor life data indicating whether some or all sensor components have expired and should be replaced, encryption information, keys, indexes to keys or hash functions, or the like, monitor or algorithm upgrade instructions or data, some or all of parameter equations, information about the patient, age, sex, medications, and other information that may be useful for the accuracy or alarm settings and sensitivities, trend history, alarm history, or the like. In an embodiment, the monitor may advantageously store data on the memory device, including, for example, measured trending data for any number of parameters for any number of patients, or the like, sensor use or expiration calculations, sensor history, or the like.

FIG. 2 also shows the patient monitor 202 including the host instrument 208. In an embodiment, the host instrument 208 communicates with the board 204 to receive signals indicative of the physiological parameter information calculated by the DSP 212. The host instrument 208 preferably includes one or more display devices 224 capable of displaying indicia representative of the calculated physiological parameters of the tissue 218 at the measurement site including for example pulse occurrence indicia In an embodiment, the host instrument 208 may advantageously comprise a handheld housing capable of displaying parameter data, including but not limited to pulse rate, plethysmograph data, perfusion quality such as a perfusion quality index ("PI™"), signal or measurement quality ("SQ"), values of blood constituents in body tissue, including for example, $SPO_2$, HbCO, HbMet, Hbt, or the like. In other embodiments, the host instrument 208 is capable of displaying values for one or more of Hbt, Hb, blood glucose, bilirubin, or the like. The host instrument 208 may be capable of storing or displaying historical or trending data related to one or more of the measured values, combinations of the measured values, plethysmograph data, or the like. The host instrument 208 also includes an audio indicator 226 and user input device 228, such as, for example, a keypad, touch screen, pointing device, voice recognition device, or the like.

In still additional embodiments, the host instrument 208 includes audio or visual alarms that alert caregivers that one or more physiological parameters are falling below predetermined safe thresholds. The host instrument 208 may include indications of the confidence a caregiver should have in the displayed data. In a further embodiment, the host instrument 208 may advantageously include circuitry capable of determining the expiration or overuse of components of the sensor 206, including, for example, reusable elements, disposable elements, or combinations of the same.

The monitor 202 also includes a mode configuration 211 accessible to the DSP 212 and responsive to inputs from, for example, the user input device 218. The mode configuration advantageously provides a caregiver the ability to configure pulse indicators in low signal quality conditions.

Although described in terms of certain embodiments, other embodiments or combination of embodiments will be apparent to those of ordinary skill in the art from the disclosure herein. For example, the monitor 202 may comprise one or more monitoring systems monitoring parameters, such as, for example, vital signs, blood pressure, ECG or EKG, respiration, glucose, bilirubin, or the like. Such systems may combine other information with intensity-derived information to influence diagnosis or device operation. Moreover, the monitor 202 may advantageously include an audio system, preferably comprising a high quality audio processor and high quality speakers to provide for voiced alarms, messaging, or the like. In an embodiment, the monitor 202 may advantageously include an audio out jack, conventional audio jacks, headphone jacks, or the like, such that any of the display information disclosed herein may be audiblized for a listener. For example, the monitor 202 may include an audible transducer input (such as a microphone, piezoelectric sensor, or the like) for collecting one or more of heart sounds, lung sounds, trachea sounds, or other body sounds and such sounds may be reproduced through the audio system and output from the monitor 202. Also, wired or wireless communications (such as Bluetooth or WiFi, including IEEE 801.11a, b, or g), mobile communications, combinations of the same, or the like, may be used to transmit the audio output to other audio transducers separate from the monitor 202. Moreover, patterns or changes in the continuous noninvasive monitoring of intensity-derived information may cause the activation of other vital sign measurement devices, such as, for example, blood pressure cuffs.

Figure 3:
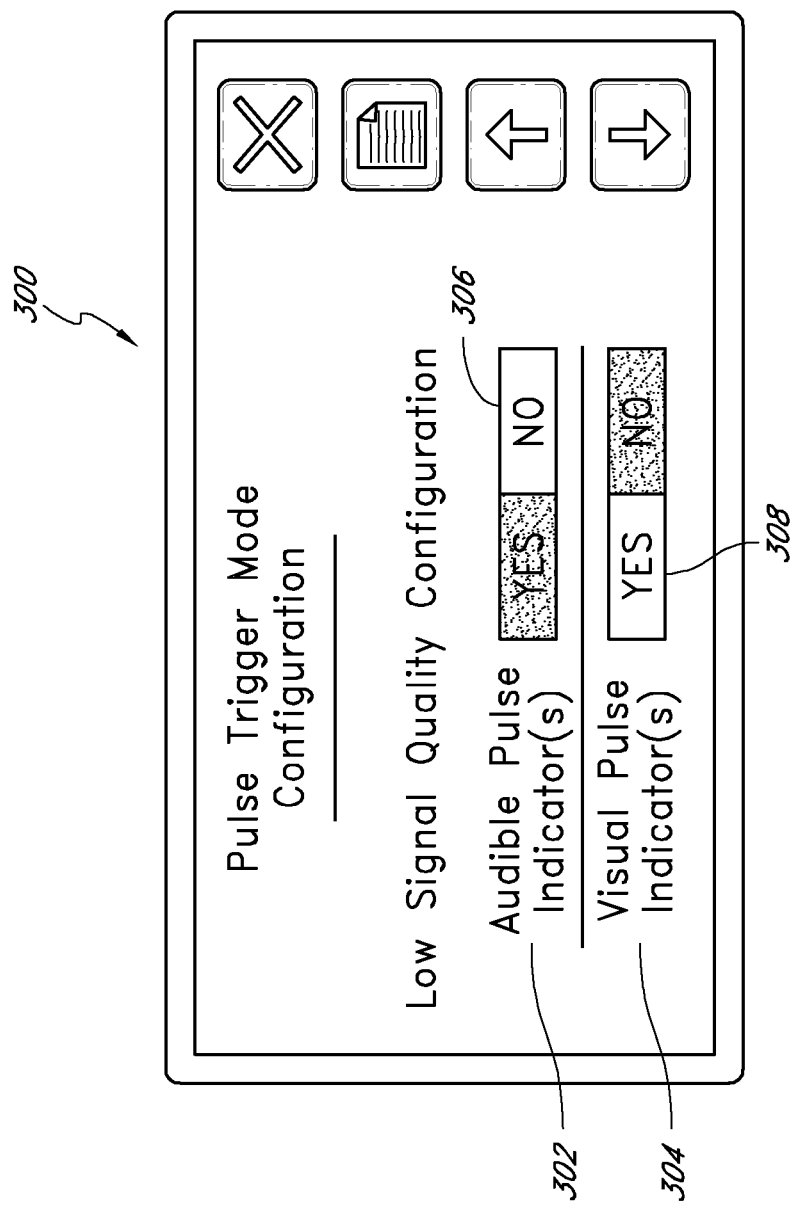
FIG. 3 illustrates an exemplary user interface providing user configuration of pulse indicators during signal distortion in one or more signals acquired from, for example, a noninvasive optical sensor, according to an embodiment of the disclosure.

FIG. 3 illustrates an exemplary user interface 300 providing user configuration of pulse indicators during signal distortion, according to an embodiment of the disclosure. In an embodiment, a user interacts with a user input device to configure certain behaviors of the patient monitor, including configuration of the audio and visual pulse indicators. As shown in FIG. 3, the interface 300 includes selectable or configurable parameters for one or both of the audible and visual pulse indicators 302, 304, respectively. For example, a user may determine that unless the instrument receives a strong signal quality, the user does not want to hear pulse indications; however, the user may want the visual indications to remain for purposes of trending, marking, closer inspection, diagnosis, or the like. In such case, the user may advantageously select "NO" 306 for the audio pulse indication configuration 302 and select "YES" 308 for the visual pulse indication configuration 304.

Although disclosed with reference to individual configuration of audio and visual pulse indications during low signal quality or confidence, an artisan will recognize from the disclosure herein a wide variety of user configurations as varying levels of detail to allow a user to customize the response of the patient monitor to varying signal quality. For example, the interface 300 may include configuration of modes governing the use of the pulse indicator amplitude for audio and visual indicators, configuration settings for a wide variety of differing audio and visual indications, such as, for example, coloring, trace characteristics, plethysmograph characteristics, trending characteristics, memory storage, varying frequencies, volume, voice messages, paging, other alarming, configuring the behavior of a bar graph, LED train, or the like.

Figure 4:
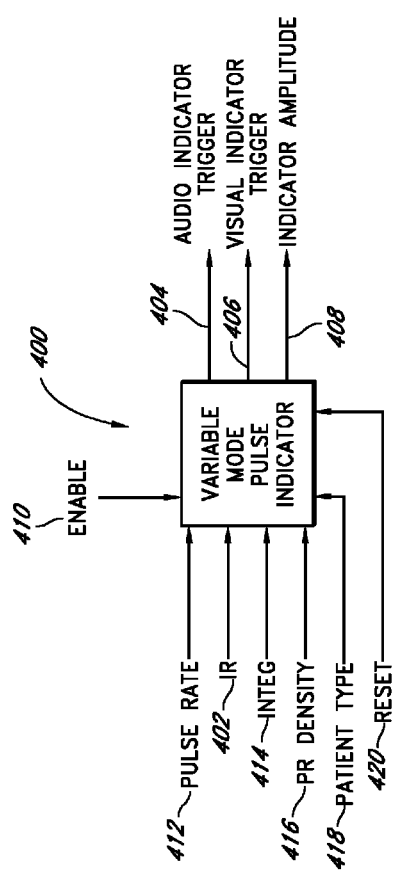
FIG. 4 illustrates exemplary inputs and outputs of a variable mode oximetry pulse indicator, according to an embodiment of the disclosure.

FIG. 4 illustrates exemplary inputs and outputs of a variable mode oximetry pulse indicator 400, according to an embodiment of the disclosure. In an embodiment, the indicator 400 can be incorporated into an oximeter to trigger the occurrence of a synchronous indication of each of the patient's arterial pulses. The indicator 400 operates on, for example, an IR signal input 402 and generates an audio trigger output 404, a visual trigger output 406, and an amplitude output 408. The output 404 can be connected to a tone generator within the oximeter monitor 202 to create, for example, a fixed-duration audible "beep" as a pulse indication. Alternatively, or in addition, the output 406 can be connected to a display generator within the oximeter monitor 202 to create one or more visual pulse indications. The visual pulse indications can include a continuous horizontal trace on a CRT, LCD display or similar display device, where vertical spikes occur in the trace synchronously with the patient's pulse. The visual pulse indications may also include a bar display, such as a vertically- or horizontally-arranged stack of LEDs or similar display device, where, for example, the bar pulses synchronously with the patient's pulse. The visual indications may include changing colors, textual or graphical information, trace data, plethysmograph data, or the like. In an embodiment, an enable signal 410 responsive to the mode configuration 211 of FIG. 4, dictates whether all, some, or none of the outputs 404, 406 and 408 are output to the audio and visual mechanisms of the host instrument 208.

FIG. 4 also shows the amplitude output 408 used to vary one or more of the audible or visual indications so as to designate input data integrity and a corresponding confidence in the parameter and pulse rate outputs of the oximeter. For example, the height of a vertical spike can be varied in proportion to the amplitude output 408, where a large or small vertical spike would correspondingly designate high or low confidence. As another example, the amplitude output 408 can be used to vary the volume of the audible beep or to change the visual indication (e.g., change color or the like) to similarly designate a high or low confidence. One of ordinary skill in the art will recognize that the trigger outputs 404, 406 and amplitude output 408 can be utilized to generate a variety of audible and visual indications of a patient's pulse and data integrity within the scope of this disclosure.

Other inputs to the variable mode pulse indicator 400 include pulse rate 412, Integ (data integrity) 414, PR (pulse rate) density 416, patient type 418 and reset 420, which are described in detail in U.S. Pat. No. '511, referenced in the foregoing. The trigger decisions involve rule-based processes that advantageously respond to the pulse waveforms of the patient's plethysmograph in low-noise or no-distortion situations. However, the trigger decisions may become dependent on the configuration parameters to determine what, if any, outputs occur and how those outputs will be audio and/or visually communicated to a caregiver.

The pulse rate input 412 to the pulse indicator 400 provides the frequency of the patient's pulse rate in beats per minute. Pulse rate can be determined as described in U.S. patent application Ser. No. 08/834,194 or U.S. patent application entitled "Plethysmograph Pulse Recognition Processor," both cited above. The Integ output 414 is a measure of the integrity of the IR 402 and Red input signals. In an embodiment, the measure is derived from signals from the sensor 206 as processed by an adaptive noise canceller. The PR density input 416 may comprise a ratio of the sum of the periods of recognizable pulses within a waveform segment divided by the length of the waveform segment. This parameter represents the fraction of the waveform segment that can be classified as having physiologically acceptable pulses. In one embodiment, a segment represents a snapshot of 400 samples of a filtered input waveform, or a 6.4 second "snapshot" of the IR waveform at a 62.5 Hz sampling rate. The derivation of Integ output 414 and PR density is described in U.S. Pat. No. 6,464,311 entitled "Plethysmograph Pulse Recognition Processor," and cited above. The patient type 418 comprises a Boolean value that indicates either an adult sensor or a neonate sensor is in use. The reset 420 initializes the state of the pulse indicator 400 to known values upon power-up and during periods of recalibration, such as when a new sensor is attached or a patient cable is reconnected.

Figure 5:
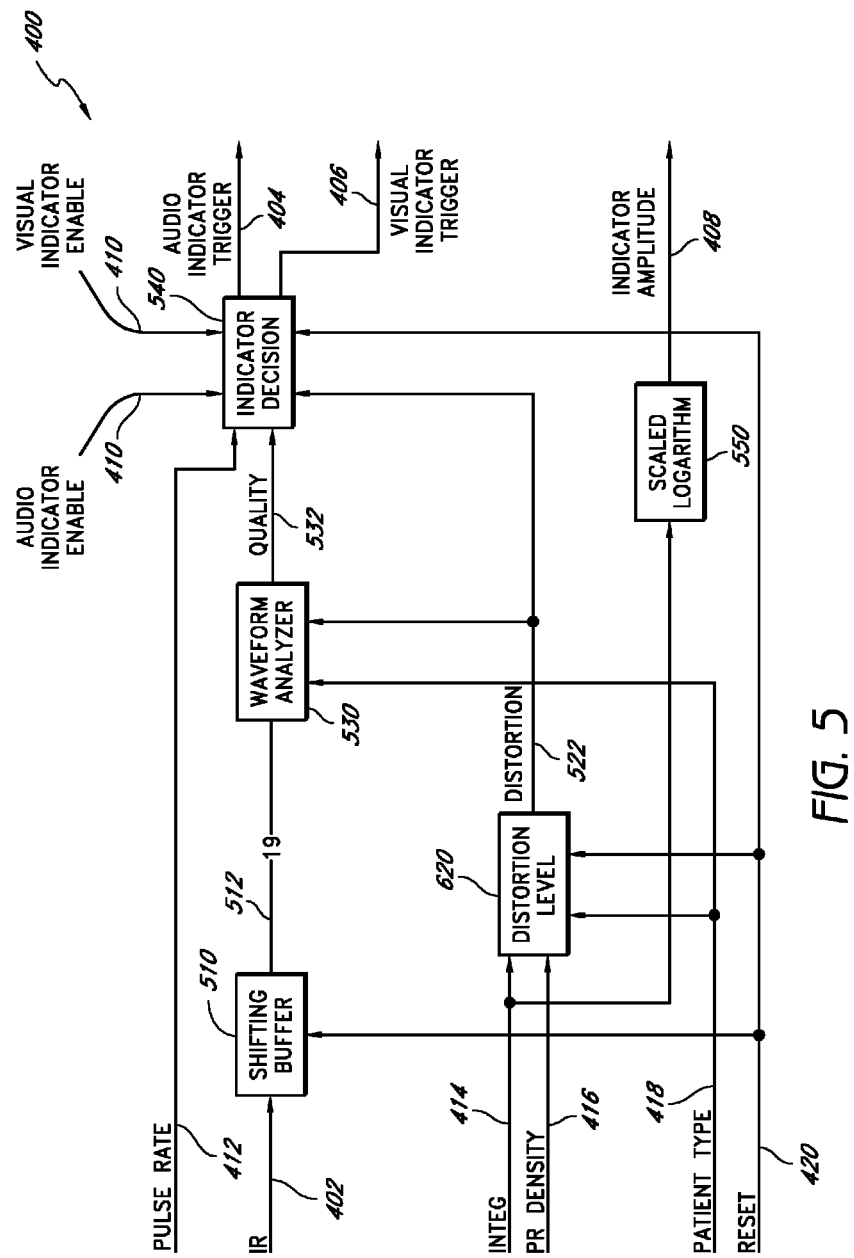
FIG. 5 illustrates an exemplary block diagram of a variable mode oximetry pulse indicator, according to an embodiment of the disclosure.

FIG. 5 illustrates an exemplary functional block diagram of a variable mode oximetry pulse indicator 400, according to an embodiment of the disclosure. As shown in FIG. 5, the indicator 400 includes a shifting buffer 510, a distortion level function 520, a waveform analyzer 530, and an indicator decision 540, which together produce the indicator triggers 404, and 406. The pulse indicator 400 also includes a scaled logarithm function 550 that produces the indicator amplitude output 408. The shifting buffer 510 accepts the IR input 402 and provides a vector output 512 representing a fixed-size segment of the patient's plethysmograph input to the waveform analyzer 530. The distortion level function 520 determines the amount of distortion present in the IR input signal 402. The inputs to the distortion level function 520 are the Integ input 414 and the PR density input 416. The distortion output 522 is a Boolean value that is "true" when distortion in the IR input 402 is above a predetermined threshold. The distortion output 522 is input to the waveform analyzer 530 and the indicator decision 540. The distortion output 522 determines the thresholds for the waveform analyzer 530. The distortion output 522 also affects the window size within which a pulse indication can occur. The distortion output 522 is also a function of the patient type input 418, which indicates whether the patient is an adult, a neonate, or the like.

In general, the waveform analyzer 530 determines whether a particular portion of the IR input 402 is an acceptable place for a pulse indication. The input to the waveform analyzer 530 is the vector output 512 from the shifting buffer 510, creating a waveform segment. A waveform segment portion meets the acceptance criteria for a pulse when it satisfies one of three conditions. These conditions are a sharp downward edge, a peak in the middle with symmetry with respect to the peak, and a peak in the middle with a gradual decline. If one of these criteria is met, the waveform analyzer "quality" output 532 is "true." Different criteria are applied depending on the state of the distortion output 522, which is also a waveform analyzer input. If the distortion output 522 indicates no distortion, strict criteria are applied to the waveform shape. If the distortion output 522 indicates distortion, looser criteria are applied to the waveform shape. Different criteria are also applied for waveforms obtained from adult and neonate patients, as indicated by the patient type 406.

The indicator decision 540 determines whether to trigger a pulse indication at a particular sample point of the input waveform. Specifically, the indicator decision 540 determines, in conjunction with the mode configuration 211, whether to, and if it is the right place to, trigger a pulse indication. The decision as to whether to trigger the pulse indication is configured by the user through the mode configuration 211. The enable signal 410 is responsive to the mode configuration 211, and, in the case one or both of the distortion and quality signals 522 and 532 indicating poor signal quality, the indicator decision 540 determines whether some, all, or none of the audio and visual triggers 404 will pass to the audio and display devices of the host instrument 208. In an embodiment, the enable signal 410 may comprise Boolean high and low signals and the mode selector may comprise logical gates configured to pass or block signals based on the enable signal 410.

In addition to the enable signals 410, the decision as to the right place to trigger a pulse indication is a function of the analyzer output 532, which is one input to the indicator decision 540. The decision as to the right time for an indicator trigger is a function of the state of the distortion output 522, which is another input to the indicator decision 540. If the distortion output 522 is "false", i.e. no distortion is detected in the input waveform, then a fixed minimum time gap from the last indicator must occur. In a particular embodiment, this minimum time gap is 10 samples. If the distortion output 522 is "true", i.e. distortion is detected in the input waveform, then the minimum time gap is a function of the pulse rate input 412. Additional details are disclosed in co-owned U.S. Pat. No. '511, referenced in the foregoing.

Figure 6:
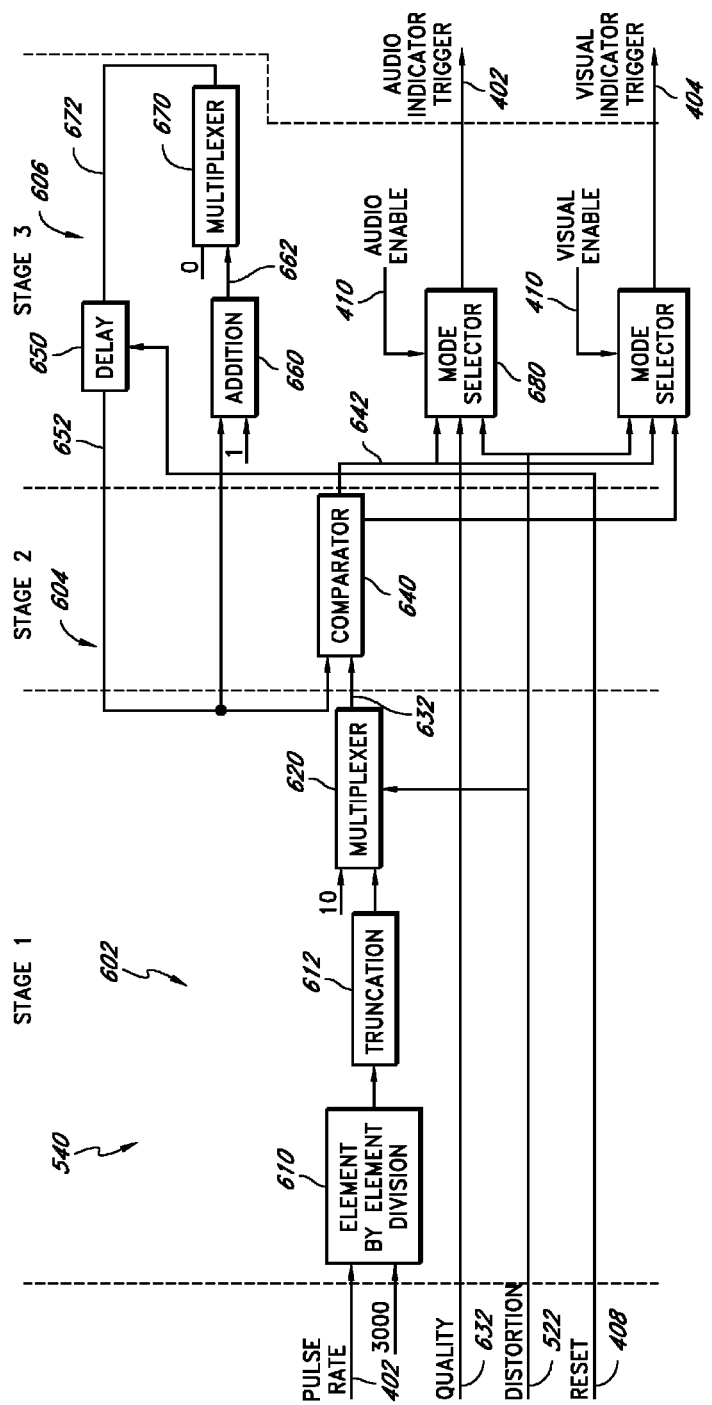
FIG. 6 illustrates an exemplary block diagram of an indicator decision module of the variable mode oximetry pulse indicator of FIG. 5, according to an embodiment of the disclosure.

FIG. 6 illustrates an exemplary block diagram of the indicator decision module 540 of the variable mode oximetry pulse indicator 400 of FIG. 5, according to an embodiment of the disclosure. As shown in FIG. 6, a first stage 602 of the indicator decision 640 determines a minimum time gap after which a pulse indicator can occur. The second stage 604 determines whether the number of samples since the last indicator is greater than the minimum allowed pulse gap. The third stage 606 decides whether to generate a pulse indicator trigger. If no trigger occurs, a sample count is incremented. If an indicator trigger occurs, the sample count is reset to zero.

The first stage 602 has a divider 610, a truncation 620 and a first multiplexer 630. These components function to set the minimum allowable gap between pulse indications. Under no distortion, the minimum gap is 10 samples. Under distortion, the gap is determined by the pulse rate. Specifically, under distortion, the minimum gap is set at about 80% of the number of samples between pulses as determined by the pulse rate input 402. This may be computed as about 0.8 times the sample frequency, such as, for example, 62.5 Hz., divided by the pulse rate in pulses per second.

The divider 610 computes 3000/pulse rate. The divider output 612 is truncated 620 to an integer value. The first multiplexer 630 selects the minimum gap as either 10 samples if the distortion input 622 is "false" or the truncated value of 3000/pulse rate if the distortion input 622 is "true." The selected value is provided on the multiplexer output 632, which is fed to the second stage 604. The second stage 604 is a comparator 640, which provides a Boolean output 642 that is "true" if a counter output 652 has a value that is equal to or greater than the minimum gap value provided at the first multiplexer output 632.

FIG. 6 also illustrates the third stage 606, which has a counter and one or more mode selector function. The counter comprises a delay element 650 providing the counter output 652, an adder 660 and a second multiplexer 670. When the counter is initialized, the second multiplexer 670 provides a zero value on the multiplexer output 672. The multiplexer output 672 is input to the delay element, which delays the multiplexer output value by one sample period before providing this value at the counter output 652. The counter output 652 is incremented by one by the adder 660. The adder output 662 is input to the second multiplexer 662, which selects the adder output 662 as the multiplexer output 672 except when the counter is initialized, as described above. The counter is initialized to zero when the pulse indicator trigger 404, 406 are "true" as determined by the output of the mode selectors 680.

The mode selectors 680 include inputs of the quality 532, the distortion 522, the enable signal 410, and the output of the comparator 642, and respectively outputs the triggers 404, 406. In an embodiment, the mode selectors 680 each comprise a logical combination of the input signals to determine the output signal. For example, a mode selector 680 may advantageously logically "OR" the quality and distortion signals 532, 522, respectively, and logically "AND" that output with the enable signal 410 and the comparator output 642. In such an embodiment, when either the quality signal 532 or the distortion signal 522 indicates less than ideal qualities in the input IR signal 402, the mode configuration 211 governs whether the output signals 404, 406 are triggered. Other embodiments could logically "AND" all the signals to require both the quality signal 532 and the distortion signal 522 to indicate poor signal quality from the sensor before the mode configuration 211 takes over. In still other embodiments, the logical combinations could be part of the mode configuration and the user may control how the signal are combined to determine whether to trigger one or more of the output signals 404, 406. Moreover, an artisan will recognize from the disclosure herein a number of logical combinations of input signals that allow the mode configuration 211 to dictate the behavior of a patient monitor with respect to at least the pulse indications when the signal quality is less than ideal.

While variable mode pulse indicator has been described, other embodiments of the present disclosure will be known to those of skill in the art from the descriptions herein. Moreover, those of skill in the art understand that information and signals can be represented using a variety of different technologies and techniques. For example, data, instructions, commands, information, signals, bits, symbols, and chips that can be referenced throughout the above description may be represented by voltages, currents, electromagnetic waves, magnetic fields or particles, optical fields or particles, or any combination thereof.

Those of skill in the art further appreciate that the various illustrative logical blocks, modules, circuits, and algorithm steps described in connection with the embodiments disclosed herein can be implemented as electronic hardware, computer software, or combinations of both. To illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans can implement the described functionality in varying ways for each particular application, but such implementation decisions should not be interpreted as causing a departure from the scope of the present invention.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or other form of storage medium known in the art. A storage medium is coupled to the processor, such that the processor can read information from, and write information to, the storage medium. In the alternative, the storage medium can be integral to the processor. The processor and the storage medium can reside in an ASIC. The ASIC can reside in a user terminal, physiological monitor and/or sensor. The processor and the storage medium can reside as discrete components in a user terminal, physiological monitor and/or sensor.

Although the foregoing disclosure has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Moreover, it is contemplated that various aspects and features of the invention described can be practiced separately, combined together, or substituted for one another, and that a variety of combination and subcombinations of the features and aspects can be made and still fall within the scope of the invention. Furthermore, the systems described above need not include all of the modules and functions described in the preferred embodiments. Accordingly, the present invention is not intended to be limited by the recitation of the preferred embodiments, but is to be defined by reference to the appended claims.

Additionally, all publications, patents, and patent applications mentioned in this specification are herein incorporated by reference to the same extent as if each individual publication, patent, or patent application was specifically and individually indicated to be incorporated by reference.

What is claimed is:

1. A patient monitor receiving a noninvasive optical sensor signal and conditionally outputting an indication of a pulse occurrence, the monitor comprising:
    an input signal from said sensor; and
    one or more signal processors configured to:
    present a caregiver with user-selectable configuration parameters that customize a trigger decision when distortion occurs in said input signal thereby providing said caregiver expected monitor behavior during at least signal distortion;
    determine a measure of distortion in said input signal; and
    determine the trigger decision based on the measured distortion and said user-selectable configuration parameters;
    said trigger decision comprising one of providing an indication of pulse occurrences even when the measured signal distortion is high, or providing no output when the signal distortion is high.

2. The patient monitor of claim 1, wherein said one or more signal processors are configured to output said indication as at least a pulse beep.

3. The patient monitor of claim 2, wherein said one or more signal processors are configured to block said pulse beep according to said user-selected configuration parameters.

4. The patient monitor of claim 2, wherein said one or more signal processors are configured to cause said pulse beep to be responsive to a statistical representation of a calculated pulse rate according to said user-selected configuration parameters.

5. The patient monitor of claim 1, wherein said one or more signal processors are configured to output said indication as at least visual display elements.

6. The patient monitor of claim 5, wherein said one or more signal processors are configured to block at least one of said display elements according to said user-selected configuration parameters.

7. The patient monitor of claim 5, wherein said one or more signal processors are configured to cause at least one of said display elements to be responsive to a statistical representation of a calculated pulse rate according to said user-selected configuration parameters.

8. A patient monitor configured to adjust its output to a predetermined expectation, the monitor comprising:
    a noninvasive optical sensor outputting a signal having a distortion quality and capable of being processed to find indications of a pulse of a wearer of the sensor;
    a memory configured to store user configuration parameters; and
    one or more processors including a plurality of modes selectable by the user configuration parameters, said one or more processors configured to:
    determine an amount of distortion associated with the signal;
    determine a pulse event from the signal; and
    determine a trigger decision corresponding to the pulse event based on a selected mode from said plurality of modes and the determined amount of distortion;
    wherein in a first mode of said plurality of modes, when said signal includes a sufficiently high amount of distortion, said trigger decision comprises not generating an auditory trigger representing the monitor's determination of a pulse event in said signal as an output to the caregiver, and
    wherein in a second mode of said plurality of modes, when said signal includes said sufficiently high amount of distortion, said trigger decision comprises generating an auditory trigger representing the monitor's determination of said pulse event in said signal as an output to the caregiver along with a visual indication that said distortion has been detected.

9. The patient monitor of claim 8, wherein said pulse event corresponds to oxygen supply in the blood.

* * * * *